United States Patent

Bloczynski et al.

[11] Patent Number: 5,310,888
[45] Date of Patent: May 10, 1994

[54] ARYLAZO CHROMOIONOPHORES

[75] Inventors: Michael L. Bloczynski, Elkhart, Ind.; Thomas Boecker, Leichlingen, United Kingdom; Paul F. Corey, Elkhart, Ind.

[73] Assignee: Miles Inc., Elkharb, Ind.

[21] Appl. No.: 964,860

[22] Filed: Oct. 22, 1992

[51] Int. Cl.$^5$ ............... C09B 29/44; G01N 31/22; G01N 33/52
[52] U.S. Cl. .................. 534/767; 534/768; 534/770; 436/74; 436/79
[58] Field of Search ............ 534/767, 768, 770; 436/74, 49

[56] References Cited

U.S. PATENT DOCUMENTS

| | | | |
|---|---|---|---|
| 4,603,209 | 7/1986 | Tsien et al. | 548/236 |
| 4,689,432 | 8/1987 | Tsien et al. | 562/435 |
| 4,795,712 | 1/1989 | Toner et al. | 436/74 |
| 4,806,604 | 2/1989 | Tsien et al. | 549/439 |
| 5,141,627 | 8/1992 | Tsien et al. | 534/564 X |

OTHER PUBLICATIONS

Grynkiewicz et al., "A New Generation of Ca$^{2+}$ Indicators with Greatly Improved Fluorescence Properties", *J. Biol. Chem.* 260(6):3440–3450 (1985).
Tsien, "New Calcium Indicators and Buffers with High Selectivity against Magnesium and Protons" *Biochemistry* 19:2396–2404 (1980).

Primary Examiner—Mary C. Lee
Assistant Examiner—Fiona T. Powers
Attorney, Agent, or Firm—Jerome L. Jeffers

[57] ABSTRACT

Disclosed are arylazo chromoionophores characterized by the formula:

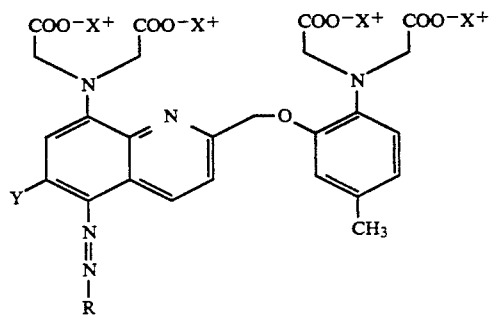

wherein X is hydrogen or a monovalent cation, Y is H or methoxy and R is a ringed aromatic organic structure which affects the optical absorption properties of the compounds. Also disclosed is a method for the detection of calcium ion using these compounds.

17 Claims, 1 Drawing Sheet

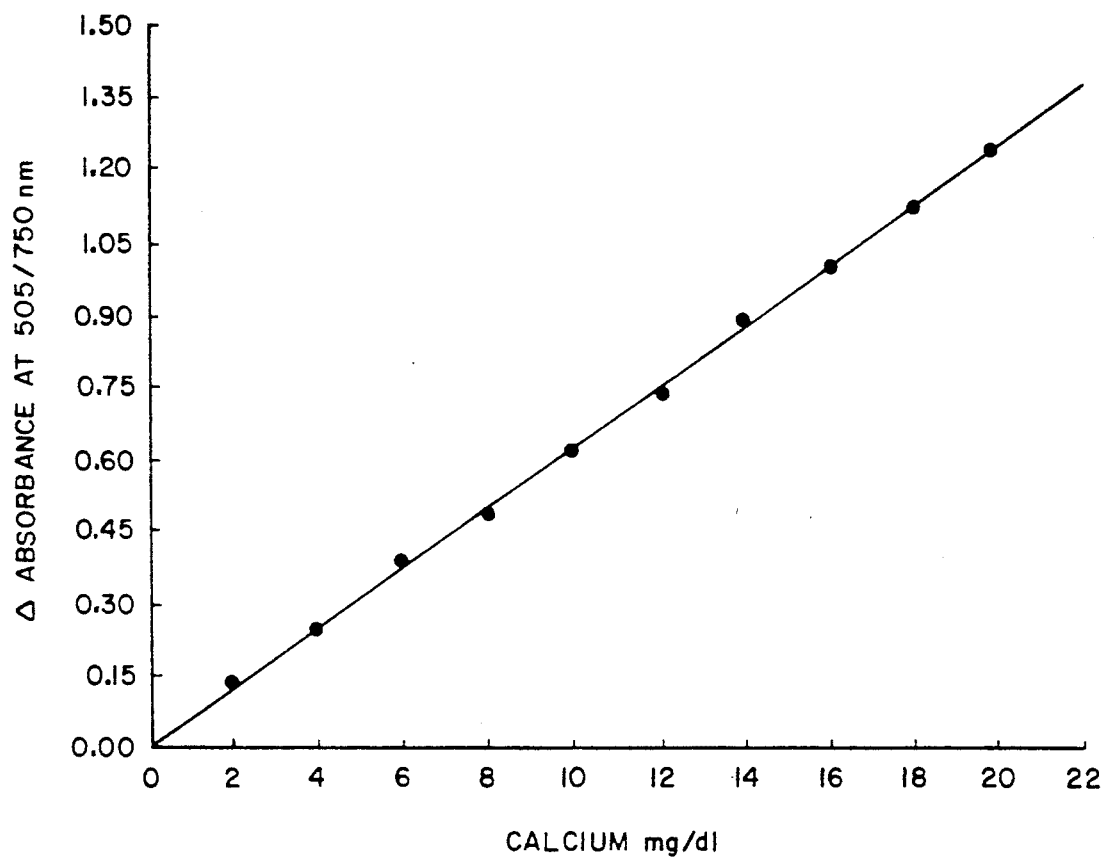

ARYLAZO CHROMOIONOPHORES

BACKGROUND OF THE INVENTION

Calcium is one of the more important elements found in the body. It is necessary not only for the skeleton but also for cells. There is, on average, about one kilogram of calcium in the human body of which 99% is located in bone with the remaining 1% distributed in plasma, extracellular fluids and intercellular compartments. This small fraction, however, plays a vital role in many biochemical and physiological functions such as a cell regulator and messenger. These functions include bone formation and homostasis, maintenance of cell membrane integrity and permeability, nerve excitation, muscular contraction and blood coagulation together with regulation of many enzyme and hormone reactions.

The concentration of calcium in body fluids, particularly in plasma, needs to be kept within a very narrow range. Its level is controlled by a number of hormones, primarily by parathyroid hormone (PTH), and calcitonin. PTH is released from the parathyroid gland in response to a decrease of calcium concentration in plasma and indirectly promotes calcium absorption in the intestine and renal tubules and increases the calcium mobilization from bone. Calcitonin, which inhibits PTH activity in bone tissue, is secreted by the thyroid gland in response to a rise in calcium ion.

Deviations from normal calcium levels occur in certain diseases. Calcium levels significantly less than normal can be indicative of hypoparathyroidism, Vitamin D deficiency or nephritis. Calcium levels of greater than normal may indicate hyperparathyroidism, Vitamin D intoxication or myeloma.

The normal value of total calcium in plasma is about 2.4 mM/L. Generally, infants have the highest calcium concentration which declines slightly with age.

The determination of calcium in serum began with the gravimetric method in which calcium was precipitated with ammonium oxalate whereupon the precipitate was dried and weighed. This method was improved upon in 1921 when there was reported a technique in which the calcium oxalate is dissolved in acid with the oxalate being determined by titration with potassium permanganate. A modification of this method, in which the washing procedure and temperature were standardized during the titration, was used as the primary procedure for calcium determination. While reasonably accurate, these procedures required large amounts of serum and were time consuming. A more sensitive and rapid complexometric titration was introduced in the 1940's which used murexide as an indicator. Several other indicators, e.g. calcon, calcein, methylthymol blue, eriochrome black T, glyoxal bis-(2-hydroxyanil) and arsenazo III, were subsequently introduced. Regardless of what indicator was used, these complexometric titration methods required a large volume of serum sample, were time consuming and suffered from a poor endpoint as well as interferences by metal ions other than calcium.

More recently, the titration method was replaced by a direct spectrophotometric method using various metallochromic indicators, the most popular of which is the ortho-cresolphthalein (CPC) complex method. In this method, calcium combines with CPC in an alkaline solution (pH 10.5 to 12) to form a deep purple calcium-dye complex. The dye's absorbance increases at 575 nm and is proportional to the concentration of calcium in the sample. A disadvantage of this method is the requirement that it be carried out at a pH in the 10 to 12 range. At this pH level, the reagent can absorb carbon dioxide resulting in baseline drift.

Arsenazo III forms colored complexes with many divalent and trivalent cations but can be used to determine micromolar quantities of calcium ion at pH 5.5 without significant interference from magnesium ion. This reagent has a high affinity for calcium ion at the physiological pH, a high extinction coefficient of the calcium-dye complex at 650 nm and exhibits high chemical stability in aqueous solutions. Accordingly it has become a useful tool for determining micromolar concentrations of calcium in single cells. While arsenazo III is widely used by researchers in studies of calcium transport in cells and cell fractions, its utility in clinical chemistry has been limited due to the presence of toxic arsenic moieties and their concomitant safety and environmental concerns.

In *Biochemistry* 19, 2396 (1980) Tsien reports the preparation of 2-[[2-bis(ethoxycarbonyl)methyl]amino]-quinoline(QUIN1) and its 6-methoxy analog (QUIN2). These compounds are described as having utility as fluorescent calcium ionophores. In a later publication, Tsien et al. describe monitoring the fluoroscence of QUIN2 as being the most popular method for measuring [$Ca^{++}$]. They go on to point out that, while QUIN2 has revealed much important biological information, its use has some inherent limitations since its preferred excitation wavelength of 339 nm is too low. It is also pointed out that its extinction coefficient (<5000) and fluorescence quantum yield (0.03 to 0.14) are also too low. In addition, autofluorescence from cells requires QUIN2 loadings of several tenths millimolar or more to obtain a satisfactory result. It is also pointed out that QUIN2 signals $Ca^{++}$ by increasing its fluorescence intensity without much shift in either excitation or emission wavelengths and that there is a need for an indicator which responds to calcium by shifting wavelengths while maintaining strong fluorescence. Another deficiency reported for QUIN2 is that its selectivity for calcium over magnesium and heavy metal divalent cations could bear improvement. This article goes on to point out that compounds having a stilbene fluorophore and an octacoordinate, tetracarboxylate pattern of liganding groups characteristic of EGTA, [(ethylene glycol bis($\beta$-aminoethyl ether)] and BAPTA, [1,2-bis (o-aminophenoxy) ethanol-N,N,N'N'-tetraacetic acid] are preferable to QUIN2. This preference is based on several factors such as improved selectivity for $Ca^{++}$ and the ability of BAPTA and EGTA to exhibit much stronger fluorescence together with wavelength shifts upon $Ca^{++}$ binding. The preparation and utility of these compounds is also disclosed in U.S. Pat. 4,603,209 to Tsien et al.

More recently Toner et al. have disclosed chromogenic derivatives of BAPTA and BAPTA like compounds in U.S. Pat. No. 4,795,712. They point out that the fluorogenic compounds of Tsien suffer from the disadvantage of adsorbing in the ultraviolet region of the spectrum, so that normal constituents of body fluids which also adsorb in the UV and short visible wavelengths tend to produce background interference with standard colorimetric equipment and procedures. They go on to say that it would be desirable to have highly selective calcium complexing compounds which would be detectable at longer wavelengths (above 400 nm) and would shift to other wavelengths when complexed with calcium to allow quantitative analysis for calcium without interference from UV and short wavelength visible light-absorbing species.

The present invention is predicated on the discovery that arylazo derivatives of QUIN1 and QUIN2 can be effectively used for the colorimetric determination of $Ca^{++}$ since they are highly selective for calcium in media which also contains magnesium ion. Further- Also included within the scope of the present invention is the use of these chromophores in the quantitative determination of calcium ion.

DESCRIPTION OF THE INVENTION

The synthesis of the chromoionophores of the present invention is illustrated by the following Scheme I in which the previously mentioned Y substituent is hydrogen.

SCHEME I

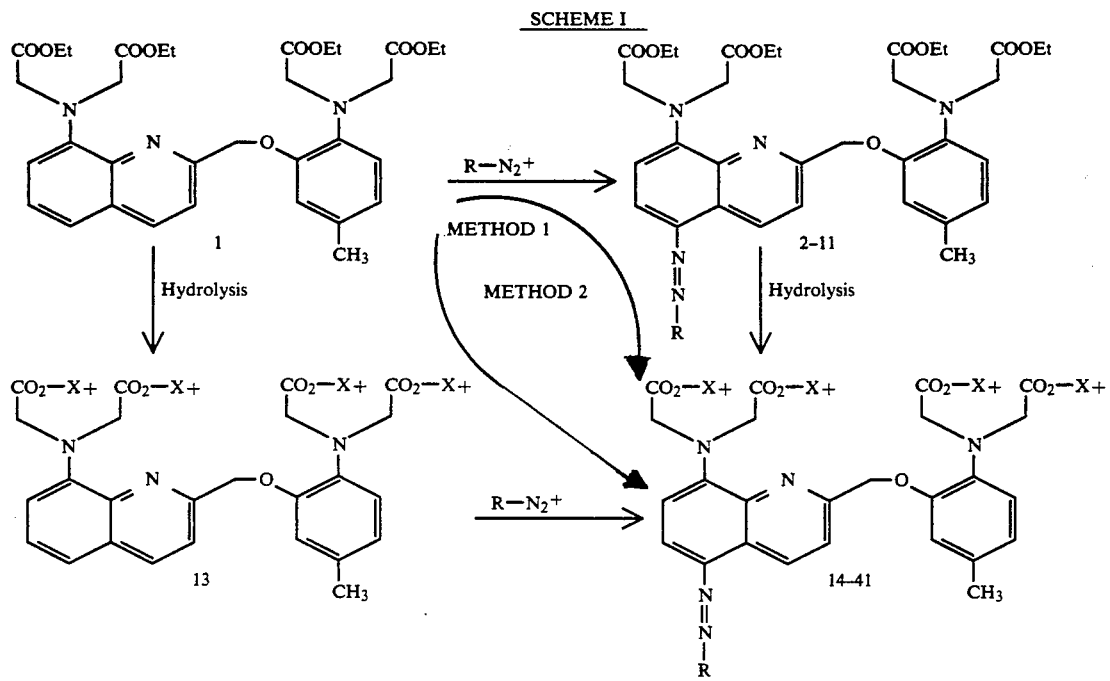

more, these compounds adsorb light at longer wavelengths than do similarly derivatized BAPTAs and exhibit a significantly greater shift in the maximum absorbance of the complexed -vs- non-complexed compound than do the corresponding chromogenic BAPTA compounds.

SUMMARY OF THE INVENTION

The present invention involves arylazo calcium chromoionophores characterized by formula A:

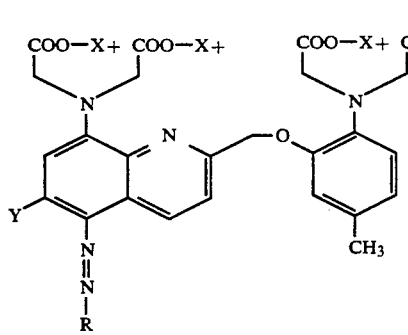

In the above formula, X is hydrogen or a monovalent cation, Y is H or methoxy and R is a five or six membered, substituted or unsubstituted aromatic or heteroaromatic ring or a fused ring system made up of five or six membered, substituted or unsubstituted, aromatic or heteroaromatic rings.

Referring to Scheme I, calcium indicators 14–41 (Table 2) are prepared using either method 1 or 2 as mentioned herein. Method 1 involves coupling of an aromatic diazonium salt $R-N_2^+$ with 1 to afford arylazotetraester intermediates 2-11 (Table 1) followed by base hydrolysis to afford the calcium indicators 14 to 23 (Table 2). In the case of QUIN2, the starting material 1 will have a 6-methoxy group.

TABLE 1

| Compound | R | Y |
|---|---|---|
| 2-12 | | |
| 2 | 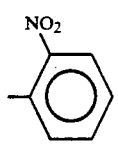 NO$_2$ | H |

TABLE 1-continued

| Compound | R | Y |
|---|---|---|
| 3 | 4-F, 3-NO₂-phenyl | H |
| 4 | 4-Cl, 3-NO₂-phenyl | H |
| 5 | 4-CF₃, 3-NO₂-phenyl | H |
| 6 | 4-CN, 3-NO₂-phenyl | H |
| 7 | 4-NO₂-phenyl | H |
| 8 | thiazolyl | H |
| 9 | 3-F, 4-NO₂-phenyl | H |
| 10 | 3-Cl, 4-NO₂-phenyl | H |
| 11 | naphthyl | H |

Structure for 51, 52:

COOEt, COOEt, COOEt, COOEt on two N-CH₂ groups attached to two phenyl rings connected by -O-CH₂-CH₂-O- linker; one phenyl bears -N=N-R, the other bears -CH₃.

TABLE 1-continued

| Compound | R | Y |
|---|---|---|
| 12 | 4-NO₂-phenyl | OCH₃ |
| 51 | 3-NO₂-phenyl | — |
| 52 | 4-NO₂-phenyl | — |

Method 2 first hydrolyses the esters of 1 to give 13 then couples this with the aromatic diazonium salt to afford indicators 24–41. Method 1 has an advantage since the arylazo-tetraester intermediates are highly crystalline and easily purified by simple recrystallization. Their base hydrolysis under preferred conditions, i.e. with a stoichiometric amount or slight excess of 4.0M KOH or LiOH in n-butyl alcohol, affords the calcium indicator compounds directly in a pure, easily collected and highly water soluble form which requires no additional purification. Method 2 has an advantage in connection with the synthesis of certain analogs labile to the base hydrolysis conditions. Some analogs can be made by either method and representative synthetic methods are given below. All starting materials are readily available to those skilled in the art of organic synthesis.

Calcium indicator compounds 43–49 (Table 2) incorporate a 6-methoxy substituent into the quinolone ring and are known in the art as QUIN2 compounds in contrast to those which are unsubstituted in the 6 position referred to as QUIN1 compounds. These may be prepared from commercially available QUIN2 free acid, compound 42, X=H, (from MTM Research Chemicals, Windham, N.H., USA) by reaction with an appropriate aromatic diazonium salt (R-N₂⁺) using method 1. Alternatively, QUIN2 tetraethylester, also available from MTM may be first coupled with an aromatic diazonium salt to give an arylazo QUIN2 tetraester (e.g. 12) which is hydrolyzed under basic conditions to give the calcium indicator compound (e.g. 48) by method 2 according to Scheme I':

SCHEME I'

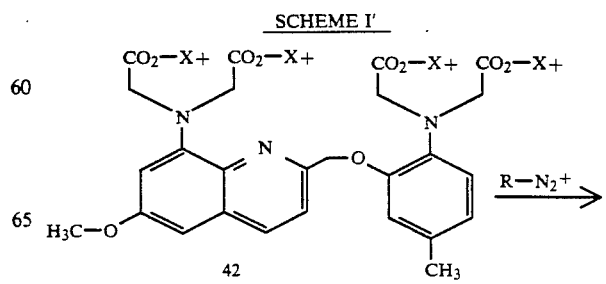

-continued
SCHEME I'
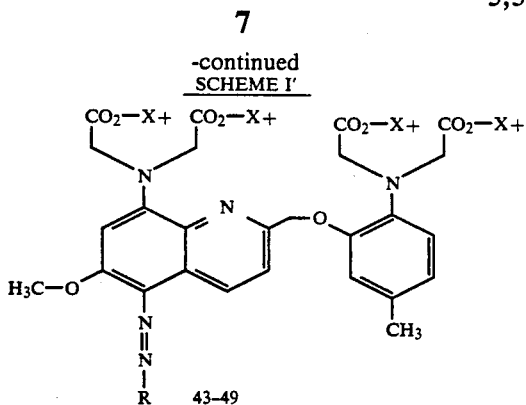
43-49
The structure and wavelengths of maximum adsorption for compounds 14-41 and 43-49 are set out in Table 2.
TABLE 2
| Compound | R | Y | X | Method | $\lambda_{max}$ (nm) pH = 9 $-Ca^{++}$ | $+Ca^{++}$ |
|---|---|---|---|---|---|---|
| 14 | 3-NO$_2$-phenyl | H | K | I | 508 | 363 |
| 15 | 3-NO$_2$-4-F-phenyl | H | K | I | 510 | 370 |
| 16 | 3-NO$_2$-4-Cl-phenyl | H | K | I | 520 | 373 |
| 17 | 3-NO$_2$-4-CF$_3$-phenyl | H | K | I | 532 | 365 |
| 18 | 3-NO$_2$-4-CN-phenyl | H | K | I | 538 | 370 |
| 19 | 4-NO$_2$-phenyl | H | K | I | 544 | 383 |
| 20 | thiazolyl | H | K | I | 548 | 404 |

TABLE 2-continued

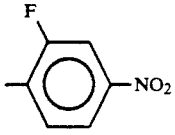

| Compound | R | Y | X | Method | λ_max (nm) pH = 9 −Ca++ | +Ca++ |
|---|---|---|---|---|---|---|
| 21 | 4-methyl-2-fluoro-nitrobenzene (F, NO$_2$) | H | K | I | 560 | 387 |
| 22 | 4-methyl-2-chloro-nitrobenzene (Cl, NO$_2$) | H | K | I | 560 | 389 |
| 23 | methylnaphthalene | H | K | I | 580 | 414 |
| 24 | 2-nitro-benzenesulfonic acid (NO$_2$, SO$_2$OH) | H | H | II | 524 | 370 |
| 25 | dichloro-sulfonamido-ethanesulfonic acid (Cl, Cl, SO$_2$NH-CH$_2$CH$_2$-SO$_2$OH) | H | H | II | 546 | 380 |
| 26 | 2-methylsulfonyl-4-nitro (SO$_2$CH$_3$, NO$_2$) | H | H | II | 594 | 396 |
| 27 | 2,4-dinitro (NO$_2$, NO$_2$) | H | H | II | 584 | 378 |
| 43 | 2-nitro-4-fluoro (NO$_2$, F) | OCH$_3$ | H | II | 508 | 404 |

TABLE 2-continued
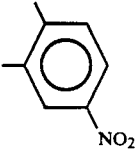
| Compound | R | Y | X | Method | λ_max (nm) pH = 9 −Ca++ | +Ca++ |
|---|---|---|---|---|---|---|
| 44 | 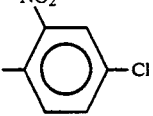 | OCH₃ | H | II | 510 | 410 |
| 45 | 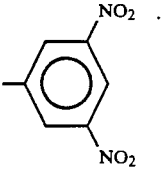 | OCH₃ | H | II | 516 | 410 |
| 46 | 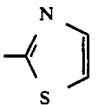 | OCH₃ | H | II | 518 | 404 |
| 47 | 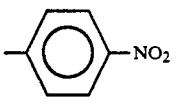 | OCH₃ | H | II | 528 | — |
| 48 | 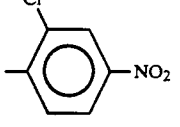 | OCH₃ | K | I | 536 | 408 |
| 49 | 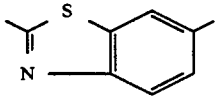 | OCH₃ | H | II | 560 | 422 |
| 28 | 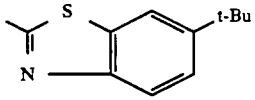 | H | H | II | 460,560 | 450 |
| 29 | | H | H | II | 575 | 432 |

TABLE 2-continued

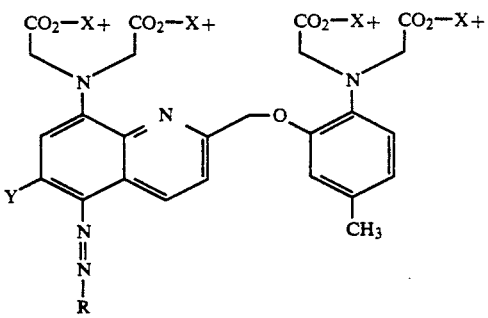

| Compound | R | Y | X | Method | λ_max (nm) pH = 9 −Ca++ | +Ca++ |
|---|---|---|---|---|---|---|
| 30 | 2-thiocarbonyl-4-chloro-3-methylphenyl | H | H | II | 576 | 420 |
| 31 | 2-thiocarbonyl-3,4-dimethylphenyl | H | H | II | 577 | 422 |
| 32 | 2-thiocarbonylphenyl | H | H | II | 580 | 414 |
| 33 | 2-thiocarbonyl-5-fluorophenyl | H | H | II | 580 | 430 |
| 34 | 2-thiocarbonyl-4-sulfophenyl | H | H | II | 580 | 420 |
| 35 | 2-thiocarbonyl-4,5-dichlorophenyl | H | H | II | 585 | 430 |
| 36 | thiocarbonyl-naphthyl | H | H | II | 588 | 486 |
| 37 | 2-thiocarbonyl-4-chloro-6-bromophenyl | H | H | II | 590 | 426 |
| 38 | 2-thiocarbonyl-5,6-dichlorophenyl | H | H | II | 592 | 422 |

TABLE 2-continued

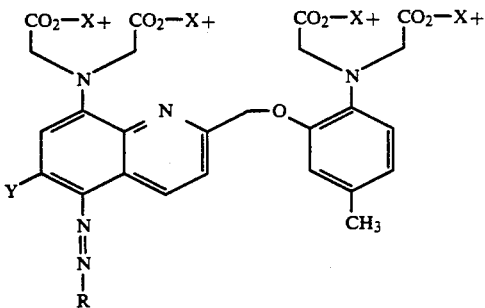

| Compound | R | Y | X | Method | λmax (nm) pH = 9 −Ca++ | +Ca++ |
|---|---|---|---|---|---|---|
| 39 | (thiazoline with 4-Cl, 6-CF3 phenyl) | H | H | II | 595 | 428 |
| 40 | (thiazoline with 4-NO2 phenyl) | H | H | II | 607 | — |
| 41 | (thiazoline with tetrachlorophenyl) | H | H | II | 600 | — |

Calcium indicating compounds such as 54-58 (Table 3) are arylazo derivatives of BAPTA as disclosed in previously mentioned U.S. Pat. No. 4,795,712. These compounds can be prepared from BAPTA tetraester compounds 50 ($Y=5-CH_3$) by the method disclosed in *J. Biol. Chem.* 260, 3440 (1985) or ($Y=4-tert-C_4H_9$) by the method disclosed in said U.S. Pat. No. 4,795,712 as illustrated in Scheme II.

SCHEME II

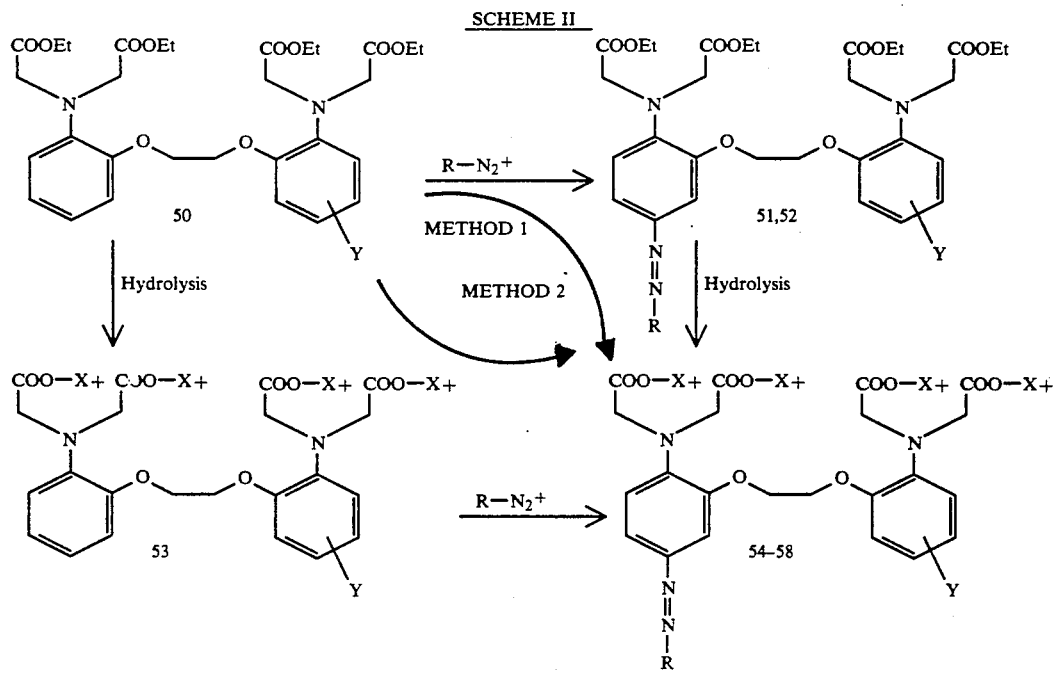

TABLE 3

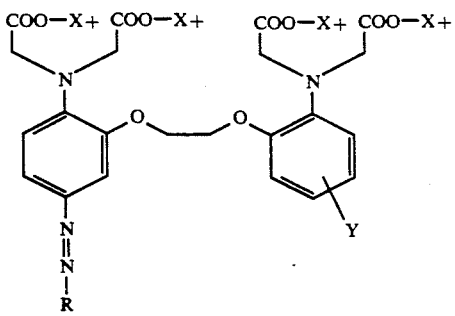

| Compound | R | Y | X | Method | λ$_{max}$ (nm) pH = 9 −Ca$^{++}$ | +Ca$^{++}$ |
|---|---|---|---|---|---|---|
| 54 | 2-NO$_2$-phenyl | 5-CH$_3$ | LI | I | 468 | 366 |
| 55 | 4-NO$_2$-phenyl | 5-CH$_3$ | LI | I | 506 | 382 |
| 56 | 2-thiazolyl | 5-CH$_3$ | H | II | 518 | 404 |
| 57 | 2,4-diNO$_2$-phenyl | 5-CH$_3$ | H | II | 540 | 388 |
| 58 | 2-SO$_2$CH$_3$-4-NO$_2$-phenyl | 4-T-BU | H | II | 576 | 424 |

The 5 arylazo-BAPTA analogs (54–58) were prepared in order to demonstrate the superior calcium indicating characteristics of the arylazo-QUIN compounds by direct comparison of BAPTA and QUIN analogs with the same substituted arylazo moieties.

Table 4 summarizes the visible spectral data for the uncomplexed (−Ca$^{++}$) and the metal-complexed (+Ca$^{++}$) indicators in pH=9.0 borate buffer as further described under performance evaluation.

TABLE 4

| | ARYLAZO-QUIN COMPOUNDS | | | | ARYLAZO-BAPTA COMPOUNDS | | | | |
|---|---|---|---|---|---|---|---|---|---|
| ARYLAZO MOIETY (R) | Compound No. | λ$_{max}$ (nm) pH = 9.0 −Ca$^{++}$ | λ$_{max}$ (nm) pH = 9.0 +Ca$^{++}$ | Δλ$_Q$ (nm) | Compound No. | λ$_{max}$ (nm) pH = 9.0 −Ca$^{++}$ | λ$_{max}$ (nm) pH = 9.0 +Ca$^{++}$ | Δλ$_B$ (nm) | Δλ$_Q$ − Δλ$_B$ (nm) |
| 2-NO$_2$-phenyl | 14 | 508 | 363 | 145 | 54 | 468 | 366 | 102 | 43 |
| 4-NO$_2$-phenyl | 19 | 544 | 383 | 161 | 55 | 506 | 382 | 124 | 37 |

TABLE 4-continued

| ARYLAZO MOIETY (R) | ARYLAZO-QUIN COMPOUNDS | | | | ARYLAZO-BAPTA COMPOUNDS | | | | |
|---|---|---|---|---|---|---|---|---|---|
| | Compound No. | $\lambda_{max}$ (nm) pH = 9.0 $-Ca^{++}$ | $\lambda_{max}$ (nm) pH = 9.0 $+Ca^{++}$ | $\Delta\lambda_Q$ (nm) | Compound No. | $\lambda_{max}$ (nm) pH = 9.0 $-Ca^{++}$ | $\lambda_{max}$ (nm) pH = 9.0 $+Ca^{++}$ | $\Delta\lambda_B$ (nm) | $\Delta\lambda_Q - \Delta\lambda_B$ (nm) |
| (N/S thiazolyl) | 20 | 548 | 404 | 144 | 56 | 518 | 404 | 114 | 30 |
| 2,4-dinitrophenyl | 27 | 584 | 378 | 206 | 57 | 540 | 388 | 152 | 54 |
| 2-methylsulfonyl-4-nitrophenyl | 26 | 594 | 396 | 198 | 58 | 576 | 424 | 152 | 46 |

Referring to Table 4, it is important to note that the arylazo-QUIN compounds exhibit a greater shift in their absorption maxima ($\Delta\lambda_{max}$) upon complexation with $Ca^{++}$ than do the corresponding arylazo BAPTA compounds of the prior art. For the five pairs of compounds set out in Table 4, the increased spectral shift ranged from 30 to 54 nm.

One skilled in the art of dye chemistry might anticipate the $\lambda_{max}$ of an uncomplexed arylazo-QUIN compound to be at a longer wavelength than that of the corresponding arylazo-BAPTA analog due to the extended conjugation afforded by the quinoline ring system. However, one could not anticipate the $\lambda_{max}$ of the metal-complexed arylazo-QUIN compound to be at the same or shorter wavelength than the arylazo-BAPTA analog. This in part accounts for the increased spectral shift of the arylazo-QUIN indicators, which increase offers significant advantages when these compounds are used as indicators in diagnostic assays for calcium in biological fluids.

It is unexpected that the arylazo-QUIN compounds are at all suitable for the determination of calcium in biological fluids, such as human blood or plasma, where calcium is present at high levels in a mixture containing other metal ions such as magnesium. Thus, in J. Biological Chem. 260, 3440 (1985) Grynkeiwicz et al. state that "the high effective affinity of QUIN2 for $Ca^{++}$ is ideal for measuring levels ... near $10^{-7}$, but also means that at the micromolar levels or above, the dye approaches saturation and loses resolution." In human blood, the levels of $Ca^{++}$ can range from 1–20 mg/dl ($2.5\times10^{-4}$ to $5\times10^{-3}$M), and even with a 1:100 dilution of the sample on a typical clinical analyzer the final $Ca^{++}$ concentration will still be $2.5\times10^{-6}$ to $5\times10^{-5}$M, which is well into the micromolar range. Unexpectedly, the arylazo-QUIN compounds of the present invention exhibit a linear response to calcium in serum over the range of 0–20 mg/dL with no loss of resolution when the sample is diluted 1:100 into the analytical reagent solution containing the indicator.

Referring again to the Grynkeiwicz et al. reference, they point out that "the selectivity for QUIN2 for calcium over magnesium could bear improvement." This is an important consideration since $Mg^{++}$ levels in human serum are typically higher than are the calcium levels and can be as high as 2.93 mg/dL ($1.2\times10^{-3}$M). Interference by $Mg^{++}$ would limit the utility of the arylazo-QUIN indicators in medical diagnostics yet we have found no significant interference at levels more than 3-fold higher using reagents incorporating compounds such as 14.

Grynkeiwicz et al. also note that "Greater selectivity for binding $Ca^{2+}$ instead of $Mg^{2+}$ is observed in related tetracarboxylate chelators in which the rings are linked by ether linkages without any quinoline ring nitrogen." Contrary to the doubts raised by this reference, we have discovered the arylazo-QUIN compounds to be very useful indicators which offer substantial advantages over prior art compounds for measuring calcium in biological samples. As noted above, the arylazo-QUIN compounds of the present invention can be illustrated by general formula A in which Y is hydrogen or methoxy, and X represents hydroge or a monovalent cation, e.g. lithium, sodium, or potassium, with potassium being the preferred specie. The R moiety can be any of a wide variety of ringed aromatic organic structures unsubstituted or substituted with moieties such as, for example, alkyl, alkoxy, halo, cyano, nitro, aryl, heteroaryl, keto or mesyl which completes the structure of the azo dye and effects the optical absorption properties of the compounds of the present invention. Typical of R are:

1. A six membered, substituted or unsubstituted carbocyclic aromatic ring. Examples of such six membered rings include 2-nitrophenyl; 2-nitro-4fluorophenyl; 2-nitro-4-chlorophenyl; 2-nitro-4trifluoromethylphenyl; 2-nitro-4-cyanophenyl; 4-nitrophenyl; 2-fluoro-4-nitrophenyl; 2-chloro-4-nitrophenyl; 3-nitro-4-sulfophenyl; 2,5-dichloro-4-(2'-sulfoethylsulfonamido)phenyl; 2-methane-sulfonyl-4-nitrophenyl; 2,4-dinitrophenyl; 2-nitro-4-fluorophenyl; 2-chloro-5-nitrophenyl; or 3,5-dinitrophenyl.

2. A five or six membered, substituted or unsubstituted heteroaromatic ring, for example, 2-thiazolyl; 4-methyl-2-thiazolyl; 4-phenyl-2thiazolyl; 4,5-dimethyl-2-thiazolyl; 4-phenyl-2thiazolyl; 5-nitro-2-thiazolyl; 5-bromo-2-thiazolyl; 4-carboxymethyl-2-thiazolyl; 5-nitrophenylsulfonyl-2-thiazolyl; 2-pyridyl; 4,6-dimethyl-2-pyridyl; 5-chloro-2-pyridyl; 5-bromo-2-pyridyl; 3-methyl-2pyridyl; 5-bromo-3-nitro-2-pyridyl; 3- chloro-5-trifluoromethyl-2-pyridyl; 3,5-dichloro-2-pyridyl; 3-nitro-2-pyridyl; 4-pyridyl; 2,5,6-trifluoro-3-chloro-4-pyridyl; 2-methoxy-5-pyridyl; 2,6-dimethoxy-3-pyridyl; 5-nitro-2-pyrimidinyl; 4-methyl-2-pyrimidinyl; 4,6-dimethyl-2-pyrimidinyl; 4,6-dimethoxy-2-pyrimidinyl; 4-chloro-6-methyl-2-pyrimidinyl; 5-methyl-3-isoxazolyl; 3-methyl-5-isoxazolyl; 3-methyl-5-isothiazolyl; 1-ethyl-5-pyrazolyl; 2-(1,3,4-thiadiazolyl); 5-ethyl-2-(1,3,4-thiadiazolyl) or 3-phenyl-5-(1,2,4-thiadiazolyl)).

3. A fused ring system made up of five or six membered, substituted or unsubstituted, aromatic or heteroaromatic rings, for example, 4-trifluoromethyl-6-chloro-2-benzothiazolyl; 1-napthyl; 6-(2'-hydroxyethyloxy)-2-benzothiazolyl; 6-tertbutyl-2-benzothiazolyl; 4-methyl-5-chloro-2-benzothiazolyl; 4,5-dimethyl-2-benzothiazolyl; 2-benzothiazolyl; 5-fluoro-2-benzothiazolyl; 6-sulfo-2-benzothiazolyl; 5,6-dichloro-2benzothiazolyl; 2-$\beta$-naphthothiazolyl; 4-bromo-6-chloro-2-benzothiazolyl; 4,5-dichloro-2-benzothiazolyl; 6-nitro-2-benzothiazolyl; 4,5,6,7-tetrachloro-2-benzothiazolyl; 1-isoquinolinyl; 5-isoquinolinyl; 6-nitro-5-quinolinyl; 5-chloro-2-benzoxazolyl; 5,6-dimethyl-2-benzothiazolyl; 6-ethoxy-2-benzothiazolyl; 6-fluoro-2-benzothiazolyl; 4-methoxy-2-benzothiazolyl; 6-methoxy-2-benzothiazolyl; 4-methyl-2-benzothiazolyl; or 6-methyl-2-benzothiazolyl.

The present invention is further illustrated by the following examples:

EXAMPLE I

The synthesis of 2-nitrophenylazo-QUIN1 tetrapotassium salt (14) and thiazolylazo-QUIN1 (20) are typical of the method 1 route used to prepare arylazo-QUIN analogs 14–23 and 48.

Step I (Synthesis of Tetraester Intermediate 2)

300 mg (2.18 mmol) 2-nitroaniline and 1.2 mL concentrated aqueous HCl were heated at 50° C. for 1 hour with stirring. The resulting paste was diluted with 3.0 mL water and cooled in an ice bath for 5 minutes. A solution of 160 mg (2.2 mmol) NaNO$_2$ in 1.0 mL water was added rapidly to the stirred solution and maintained in the ice bath for 1 hour. The clear, almost colorless solution was added dropwise over about 2 minutes to a stirred solution of 1.25 g (2.0 mmol) QUIN1 tetraethyl ester (1) (prepared according to the method of Tsien, *Biochemistry* 19, 2396, 1980) in 40 mL CH$_3$OH maintained at $-10°$ C. The reaction mass was stirred at $-10°$ C. for 30 minutes and allowed to warm to ambient temperature and stirred overnight. The solid that separated from the reaction mixture was filtered, washed with 250 mL CH$_3$OH/H$_2$O (1:1), stirred in 60 mL CH$_3$OH for 1 hour at ambient temperature and filtered again. The crude product was dissolved in 50 mL ethyl acetate (EtOAc) and diluted with 100 mL hexane whereupon a solid rapidly fell from the solution. The mixture was refrigerated overnight at about 0° C.; the solid was collected by filtration, washed with hexane and vacuum dried at 65° C. to afford the 2-nitrophenylazo-QUIN1 tetraethyl ester intermediate compound (1.18 g 76.6%) as brick-red fine needles with mp $=120°-121.5°$ C.

Rf$=0.4$ on silica gel tlc plates developed in EtOAc/hexane (4:6). IR(KBr) cm$^{-1}$ 3443, 2983, 1748, 1559, 1531, 1514, 1487, 1402, 1364, 1306, 1262, 1185, 1027; $^1$H NMR (CDCl$_3$) $\delta$ 9.30 (d, J$=8.8$Hz, 1H), 8.02 (d, J$=8.8$Hz, 1H), 7.82–7.92 (m, 3H), 7.68 (t of d, J$_t=7.7$Hz and J$_d=1.4$Hz, 1H), 7.52 (t of d, J$_t=7.7$Hz, and J$_d=1.3$Hz, 1H), 6.95 (d, J$=8.8$Hz, 1H), 6.88 (d, J$=8.0$Hz, 1H), 6.75 (d, J$=1.3$Hz, 1H), 6.70 (br d, J$=8.0$Hz, 1H), 5.33 (s, 2H), 4.56 (s, 4H), 4.31(q, J$=7.1$Hz, 4H), 4.22 (s, 4H), 3.56 (q, J$=7.1$Hz, 4H), 2.24 (s, 3H), 1.32 (t, J$=7.1$Hz, 6H), 1.20 (t, J$=7.1$Hz, 6H); $^{13}$C NMR (CDCl$_3$) ppm 171.5, 170.9, 155.0, 150.5, 150.3, 147.4, 145.8, 140.0, 139.0, 136.7, 133.0, 132.6, 129.4, 128.5, 123.9, 122.0, 120.6, 120.1, 119.1, 115.7, 114.4, 112.4, 71.4, 61.2, 60.6, 59.3, 54.0, 20.9, 14.3, 14.2.

Anal. Calcd. for C$_{39}$H$_{44}$N$_6$O$_{11}$: C, 60.61; H, 5.74; N, 10.88 Found: C, 61.00; H, 5.80; O, 11.02.

Step 2 (Synthesis of 14, X=K)

1.000 g (1.294 mmol) 2-nitrophenylazo-QUIN1 tetraethyl ester (2) and 35 mL n-butyl alcohol (n-BuOH) were stirred in a 100 mL recovery flask at ambient temperature under Argon for 10 minutes. The suspension was then treated with 1.54 mL (6.16 mmol, 4.75 equivalents) of 4.00M aqueous KOH (high purity semiconductor grade) and an additional 7 mL n-BuOH and allowed to stir at ambient temperature under argon overnight. After 23 hours tlc (silica gel; n-BuOH/acetic acid (HOAc)/H$_2$O (4:1:1) product R$_f=0.16$, starting material R$_f=0.95$) indicated that the reaction was complete. The reaction mass was transferred to a centrifuge tube using about 2 mL n-BuOH to rinse the flask and then centrifuged at 20,000$\times$G for 10 minutes whereupon the supernatant was pipetted from the resulting pellet and discarded. The pellet was twice resuspended with sonication in 20 mL n-BuOH and centrifuged as above. The final pellet was vacuum dried overnight at ambient temperature in the centrifuge tube, powdered and transferred to a vial where it was vacuum dried for an additional 2 days at ambient temperature to give 1.03 g (90%) of the title compound (14) as a brick-red powder which retained traces of the solvent used in the workup.

IR (KBr) cm$^{-1}$ 3442 (broad), 2928, 1597, 1507, 1397, 1286, 1241, 1182; H NMR (D$_2$O) $\delta$ 9.20 (d, J$=8.9$Hz, 1H), 8.04 (d, J$=8.1$Hz, 1H), 7.96 (d, J$=8.9$Hz, 1H), 7.79–7.90 (m, 3H), 7.62 (t of d, J$_t=7.7$Hz and J$_d=1.5$Hz, 1H), 6.83–6.90 (m, 2H), 6.70–6.79 (m, 2H), 5.41 (s, 2H), 4.42 (s, 4H), 3.95 (s, 4H), 2.16 (s, 3H); $^{13}$C NMR (D$_2$O) ppm 182.3, 181.3, 157.7, 154.8, 152.1, 148.7, 148.0, 141.2, 140.9, 140.2, 136.8, 135.2, 134.5, 132.2, 131.2, 127.2, 124.4, 123.4, 122.7, 121.1, 119.6, 117.2, 114.4, 73.7, 62.0, 59.8, 22.7.

Anal. Calcd. for C$_{31}$H$_{24}$N$_6$O$_{11}$K$_4$·½n-BuOH·3H$_2$O Theory C, 43.40; H, 3.70; N, 9.49 Found: C, 43.27; H, 3.92; N, 9.28.

EXAMPLE II

Synthesis of Thiazolylazo-QUIN1 (20, X=K)

Step 1 (Synthesis of Tetraester Intermediate 8)

A 1.0 mL mixture of H$_2$SO$_4$/H$_2$O (7:3, v/v) was cooled in an ice bath and NaNO$_2$ (44.8 mg, 0.65 mmol) was added. A solution of 2-aminothiazole (66 mg, 0.65 mmol) in 0.5 mL HOAc was added dropwise, the mixture was stirred at 0°–5° C. for 1.5 hours and then diluted with 1.0 mL H$_2$O. After stirring an additional 40 minutes the resulting solution of the diazonium salt was added dropwise, over 15 minutes, to a solution of 1 (250 mg, 0.4 mmol) in 5.0 mL ice cold CH$_3$OH. The mixture was allowed to stir at 0°–5° C. for 1 hour and then diluted with 75 mL H$_2$O. The orange-red solid that separated was collected by filtration, washed with 100 mL H₂O and dried to give 8 (220 mg, 75%). Recrystallization from EtOAc/hexane (1:3, v/v) afforded the analytical sample as an orange-red powder having a mp of 100°-102° C.

IR (CHCl₃) cm⁻¹ 3001, 2933, 1744, 1559, 1506, 1487, 1412, 1373, 1309, 1258, 1192, 1139, 1109, 1024; ¹H NMR (CDCl₃) δ 9.19 (d, J=9.2Hz, 1H), 8.39 (d, J=9.2Hz, 1H), 7.99 (d, J=3.5Hz, 1H), 7.92 (d, J=8.8Hz, 1H), 7.35 (d, J=3.8Hz, 1H), 6.86-6.91 (m, 2H), 6.68-6.73 (m, 2H), 5.26 (s, 2H), 4.66 (s, 4H), 4.33 (q, J=7.1Hz, 4H), 4.21 (s, 4H), 4.12 (q, J=7.1Hz, 4H), 2.23 (s, 3H), 1.34 (t, J=7.1 Hz, 6H), 1.21 (t, J=7.1 Hz, 6H); ¹³C NMR (CDCl₃) ppm 171.4, 170.6, 155.2, 151.2, 150.3, 143.4, 138.95, 138.89, 136.7, 133.0, 132.4, 128.7, 122.0, 120.8, 120.1, 119.9, 116.4, 114.4, 112.5, 71.3, 61.3, 60.6, 56.4, 54.0, 20.9, 14.24, 14.20.

Anal. Calcd. for C₃₆H₄₂N₆O₉S: C, 58.84; H, 5.76; N, 11.44 Found: C, 58.85; H, 5.70; N, 11.63.

Step 2

A suspension of 8 (0.144 g, 0.196 mmol) in n-BuOH (8.8 mL) at ambient temperature was treated with 4.0M KOH (0.245 mL, 0.98 mmol, 5 eq) and allowed to stir for 7 hours. The reaction mixture was then cooled at 5° C. for 17 hours, transferred to a centrifuge tube with a few mL n-BuOH and centrifuged at 7500×G for 20 minutes. The supernatant was discarded, whereupon the resulting pellet was resuspended with sonication in about 3 mL fresh n-BuOH and centrifuged again. The product was washed with EtOAc and hexane by resuspension/centrifugation and vacuum dried (0.1 torr) at 60° C. for 2 hours to afford 20 (0.133, 87%) as the dark purple tetrapotassium salt.

IR (KBr) cm⁻¹ 3418 (broad), 1587, 1505, 1396, 1287, 1247, 1202, 1179, 1136, 1022; ¹H NMR (D₂O) δ 9.15 (d, J=8.9Hz, 1H), 8.07 (d, J=9.3Hz, 1H), 7.81 (d, J=3.5Hz, 1H), 7.72 (d, J=8.9Hz, 1H), 7.43 (d, J=3.5Hz, 1H), 6.82 (d, J=9.3Hz, 1H), 6.76 (d, J=0.7Hz, 1H), 6.62-6.70 (m, 2H), 5.31 (s, 2H), 4.40 (s, 4H), 3.87 (s, 4H), 2.10 (s, 3H); ¹³C NMR (D₂O) ppm 182.5, 180.6, 157.8, 156.0, 152.1, 145.0, 141.1, 140.3, 139.6, 135.3, 134.2, 132.0, 124.3, 123.7, 123.0, 121.0, 120.6, 117.2, 114.8, 73.6, 62.4, 59.7, 22.7.

Anal Calcd. for C₂₈H₂₂N₆O₉SK₄·½n-BuOH·3H₂O: Theory: C, 41.60; H, 3.84; N, 9.70 Found: C, 41.77; H, 3.81; N, 9.89.

The synthesis of benzothiazolyl-QUIN1 tetraacid (32) and (4-trifluoromethyl-6-chlorobenzothiazoyl)-QUIN1 tetraacid (39) as described below are typical of the method 2 route used to prepare arylazo-QUIN1 analogs 24–41.

EXAMPLE III (Synthesis of Benzothiazolylazo-QUIN1 Tetraacid 32)

Step 1 (Synthesis of QUIN1 Tetraacid (13, X=H)

6.24 g (10 mmol) of QUIN1 tetraethyl ester (1) was dissolved in 100 mL EtOH and treated with a 5 molar excess of aqueous 4M KOH. The reaction mixture was stirred for 16 hours at 40° C. after which time the reaction was judged complete by tlc (silica gel; EtOH:-HOAc:H₂O (4:1:1). After the addition of 100 mL H₂O the EtOH was evaporated under reduced pressure and the solution pH was adjusted to 2.5 by addition of 1M HCl. The tetraacid started precipitating out half crystalline/half gummy. A totally crystalline product was isolated after stirring for 24 hours. ¹H NMR (CD₃OD) δ 8.22 (d, 1H), 7.67 (d, 1H), 7.40 (d, 2H), 7.07 (t, 1H), 6.85 (d, 1H), 6.84 (s, 1H), 6.66 (d of d, 1H), 5.35 (s, 2H), 4.30 (s, 4H), 4.07 (s, 4H), 2.18 (s, 3H).

Anal. Calcd. for C₂₅H₂₅N₃O₉: C, 58.71; H, 4.93; N, 8.22 Found: C, 58.75; H, 4.89; N, 8.34.

Step 2 (Diazotization)

220 mg (1.46 mmol) 2-aminobenzothiazole was dissolved in a mixture of 15 mL H₃PO₄ and 5 mL HOAc with sonication, cooled to 0° C. and treated with 0.25 mL of 40% nitrosylsulfuric acid. The reaction was stirred for 2 hours at 0° C. followed by the addition of a small amount of urea. After stirring for an additional 1 hour, the solution was ready for use in Step 3.

Step 3 (Coupling)

0.747 g (1.46 mmol) QUIN1 tetraacid (13, X=H) was dissolved in a mixture of 100 mL CH₃OH and 50 mL H₂O, cooled to −20° C. and treated with the diazonium solution from Step 2. The reaction mixture was maintained at pH 4 by the addition of concentrated NaOH. The solution was warmed to ambient temperature and the pH was adjusted to 2.5. The CH₃OH was removed by evaporation under reduced pressure and the product (32) was collected by filtration. Yield: 0.9 g (91%).

Step 4 (Purification)

Impure 32 was purified by flash chromatography on a RP-2 silica gel column (Silica Gel 60 Silanized, particle size 0.063-0.200 mm; from E. Merck) packed and developed with a solvent mixture of CH₃OH/H₂O (2:3) adjusted to pH 9 with KOH. Before column application the tetraacid was suspended in a minimum volume of the developing solvent and treated with a 4 molar excess of 4M KOH to obtain a homogenous solution. Column fractions containing pure product are collected and acidified to pH 2.5; the CH₃OH was removed under reduced pressure and pure 32 was isolated by filtration.

¹H NMR (CD₃OD+DMSO-d⁶) δ 9.20 (d, 1H), 8.21 (d, 1H), 8.03 (d, 1H), 8.00 (d, 1H), 7.96 (d, 1H), 7.54 (t, 1H), 7.46 (t, 1H), 7.04 (d, 1H), 6.89 (d, 1H), 6.81 (d, 1H), 6.69 (d of d, 1H), 5.33 (s, 2H), 4.67 (s, 4H), 4.13 (s, 4H), 2.23 (s, 3H).

Anal. Calcd. for C₃₂H₂₈N₆O₉S: C, 57.14; H, 4.20; N, 12.50. Found: C, 57.32; H, 4.26; N, 12.71.

EXAMPLE IV

Synthesis of (4-trifluoromethyl-6-chlorobenzothiazolylazo)-QUIN1 Tetraacid (39)

Step 1

2-amino-4-trifluoromethyl-6-chlorobenzothiazole was diazotized as described above for the preparation of 32.

Step 2

QUIN1 tetraacid (13) was coupled with the diazonium solution prepared in Step 1 according to the procedure used for the preparation of 32, except that the coupling was done at −60° C. and there was no control of the reaction pH. Yield: 84%.

Step 3

RP-2 column purification of 39 was the same as described above for the purification of 32. ¹H NMR (CD₃OD+DMSO-d⁶) δ 9.15 (d, 1H), 8.45 (d, 1H), 8.29 (d, 1H), 8.07 (d, 1H), 7.84 (d, 1H), 7.08 (d, 1H), 6.86 (d, 1H), 6.73 (d, 1H), 6.62 (d of d, 1H), 5.32 (s, 2H), 4.73 (s, 4H), 4.04 (s, 4H), 2.19 (s, 3H).

Anal. Calcd. for $C_{33}H_{26}ClF_3N_6O_9S$: C, 51.13; H, 3.38; N, 10.84 Found: C, 51.38; H, 3.47; N, 10.63.

EXAMPLE V

The synthesis of 2-nitrophenylazo BAPTA analog 54 and thiazolyl-BAPTA analog 56 are typical of the two routes used to prepare arylazo BAPTA analogs compounds 54–58.

Synthesis of 51

0.110 g (0.19 mmol) 50 (Y=5—CH₃) [prepared as described by Grynkeiwicz in *J. Biol. Chem.* 260, 3440 (1985)] was dissolved in 75 mL CH₃OH, filtered and cooled to −40° C. whereupon 2-nitrobenzenediazonium tetrafluoroborate (0.048g, 0.2 mmol) [prepared as described by Doyle and Bryker in *J. Org. Chem.* 44, 1572 (1979)] was added at once followed by 5 mL acetone. The reaction was warmed to −20° C., allowed to stir at this temperature for 2 hours and then warmed to ambient temperature. The reaction mixture evaporated to dryness under reduced pressure and purified by chromatography (silica gel); development with hexane/EtoAc (7:3, v/v) to afford 51 (23 mg, 16%) as an orange solid with mp=105-6° C.

¹H NMR (CDCl₃) δ 7.89 (br d, J=8.1Hz 1H), 7.44-7.69 (m, 5H), 6.75-6.84 (m, 2H), 6.66-6.70 (m, 2H), 4.35-4.42 (m, 2H), 4.28-4.35 (m, 2H), 4.25 (s, 4H), 4.13 (s, 4H), 4.08 (q, J=7.1Hz, 4H), 4.06 (q, J=7.1Hz, 4H), 2.26 (s, 3H), 1.16 (t, J=7.1Hz, 6H), 1.15 (t, J=7.1Hz, 6H); ¹³C NMR (CDCl₃) ppm 171.5, 170.9, 150.3, 150.0, 147.2, 143.8, 137.1, 132.9, 132.1, 129.5, 124.0, 122.3, 122.2, 122.0, 121.5, 119.5, 118.7, 118.6, 117.1, 117.0, 114.7, 105.1, 77.8, 77.7, 67.5, 67.0, 61.3, 61.1, 60.9, 60.7, 53.9, 53.7, 20.9, 14.1, 14.0; MS [EI, direct inlet] m/z (relative intensity) 751 (11.7%, M⁻⁺), 678 (100%).

Synthesis of 54

7.52 mg (0.01 mmol) 51 in 0.5 mL n-BuOH was treated with 17.5 μL (7 eq) of 4M LiOH and stirred at ambient temperature for 17.3 hours. The reaction mixture was transferred to a micro centrifuge tube and spun at 7,000×G for 5 minutes. The supernatant was discarded and the resulting pellet was washed with 0.5 mL n-BuOH followed by 1.0 mL EtOAc using resuspension and centrifugation whereupon it was vacuum dried to give 54 (5.1 mg, 77%) as a brick-red powder.

¹HNMR (D₂O) δ 8.09 (d of d, J=8.2 Hz and J₂=1.1 Hz, 1H), 7.82 (t of d, J$_t$=7.7 Hz and J$_d$=1.2 Hz, 1H), 7.62 (t of d, J$_t$=7.8 Hz and J$_d$=1.3 Hz, 1H), 7.48-7.57 (m, 2H), 7.46(d, J=2.2 Hz, 1H), 6.97 (s, 1H), 6.7-6.80 (m, 3H), 4.40 (s, 4H), 4.05 (s, 4H), 3.73 (s, 4H), 2.25 (s,3H); ¹³C NMR (D₂O) ppm 182.6, 181.5, 152.5, 151.6, 148.0, 147.3, 140.6, 137.5, 135.1, 132.4, 128.8, 127.7, 125.1, 125.0, 122.9, 121.7, 118.1, 109.5, 70.5, 69.9, 60.2, 60.0, 22.7.

Synthesis of 53 (Y=5-CH₃, X=Li)

0.6026 g (1.0 mmol) 50 (Y=5-CH₃) was suspended in 50 mL m-BuOH, treated with 4M LiOH (1.75 mL, 7 eq) and left to stir at ambient temperature for 16 hours. The white solid product was isolated by centrifugation at 7,000×G, washed with 10 mL n-BuOH followed by 15 mL EtOAc and vacuum dried to afford 53 (Y=5-CH₃, X=Li) in quantitative yield.

IR (KBr) cm⁻¹ 3440 (broad), 2928, 1599, 1500, 1412, 1325, 1250, 1158, 1130, 1041, 985, 925; ¹H NMR (D₂O) δ 7.10-7.14 (m, 1H), 6.90-7.00 (m, 3H), 6.75-6.85 (m, 3H), 4.37 (s, 4H), 3.87 (s, 4H), 3.82 (s, 4H), 2.27 (s, 3H);

¹³C NMR (D₂O) ppm 182.6, 152.6, 152.4, 143.3, 140.6, 135.1, 124.9, 124.3, 121.4, 121.0, 118.0, 117.8, 70.4, 70.1, 60.1, 59.8, 22.7.

Anal. Calcd. for $C_{23}H_{22}N_2O_{10}Li_4 \cdot LiOH \cdot 3H_2O$ Theory: C, 46.65; H, 4.94; N, 4.73 Found: C, 46.32; H, 4.82; N, 4.52.

Synthesis of 56

2-Aminothiazole (20 mg, 0.2 mmol) was dissolved in 200 μL HOAc and added dropwise to a stirred mixture of nitrosylsulfuric acid (32 mg, 0.25 mmol) and HOAc (200 μL) maintained in an ice bath. The mixture was stirred for 45 minutes after which a small amount of urea was added. After an initial 5 minutes the mixture was added dropwise to a stirring solution of 53 (60 mg, 0.1 mmol) in 1.0 mL H₂O and 0.25 mL CH₃OH, maintained at 0°-5° C. and allowed to react for 3 hours. The reaction mixture was extracted 4 times with 1 mL portions of EtOAc and the combined extracts were dried over MgSO₄ and evaporated to dryness under reduced pressure to give 56 (42 mg, 70%). RP-2 column chromatography (as per Step 4 in the synthesis of 32) afforded pure product.

¹H NMR (DC₃OD) δ 7.95 (d, J=3.3 Hz, 1H), 7.57-7.65 (m,3H), 6.77-6.90 (m, 3H), 6.68 (d, J=7.8 Hz, 1H), 4.84 (s, 4H; COOH), 4.25-4.50 (m, 4H), 4.30 (s, 4H), 4.07 (s, 4H), 2.27 (s, 3H).

Determination of Absorption Maxima

The optical absorption maxima of the uncomplexed and complexed forms of calcium indicator compounds 14– 41 and 43–49 were determined in pH 9 borate buffer. Sufficient indicator was dissolved in the buffer to produce absorbance from about 1.0 to 2.0 when measured with a UV/VIS spectrometer. For standard curvettes with 1 cm path length and 4.0 mL volume there was typically 0.15 mg to 0.35 mg of the indicator in 4.0 mL of buffer. The uncomplexed absorption maxima was determined, then about 2.0 mg of CaCl₂ (a 50 to 100 fold molar excess) was added and the complexed absorption maximum was determined.

Performance Evaluation

The performance of 14 was evaluated in a liquid reagent formulation on a Technicon AXON ® analyzer. The reagent was composed of 100 mM borate buffer containing 100 mg/L of compound 14. Instrument parameters were as follows:

| R1 Volume | 350 μL |
| --- | --- |
| Sample Volume | 4 μL |
| Rinse Volume | 50 μL |
| Delay | 3 minutes |
| Filter | 505/750 nm |
| Type | End-point/A Decrease |

Linearity was assessed using aqueous calcium solutions ranging in concentration from 0–20 mg/dL. The figure which plots calcium concentration versus the change in absorbance at 505 nm, illustrates the linearity of the response.

Multiple linear regression analysis of the data in FIG. 1 yields the equation:

$$Y = 0.0625X - 0.001$$

where Y is the Δ absorbance at 505 nm divided by the absorbance at 750 nm and X is the calcium concentration in mg/dL. The correlation coefficient (R) is 0.9997.

What is claimed is:

1. An arylazo chromoionophore characterized by the formula:

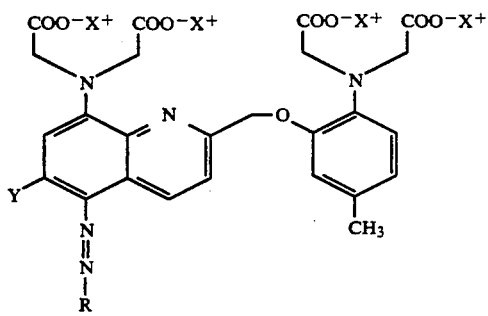

wherein X is hydrogen or a monovalent cation, Y is H or methoxy and R is a ringed aromatic organic structure which completes the structure of the azo dye.

2. The arylazo chromoionophore of claim 1 wherein R is a five or six membered, substituted or unsubstituted carbocyclic aromatic or heteroaromatic ring or a fused ring system made up of five or six membered, substituted or unsubstituted, carbocyclic aromatic or heteroaromatic rings.

3. The arylazo chromoionophore of claim 1 wherein the carbocyclic aromatic or heteroaromatic ring is substituted with alkyl, alkoxy, halo, cyano, nitro, aryl, heteroaryl, keto or mesyl moieties.

4. The arylazo chromoionophore of claim 2 wherein R is a substituted six membered carbocyclic aromatic ring selected from the group consisting of 2-nitrophenyl; 2-nitro-4-fluorophenyl; 2-nitro-4-chlorophenyl; 2-nitro-4-trifluoromethylphenyl; 2-nitro-4-cyanophenyl; 4-nitrophenyl; 2-fluoro-4-nitrophenyl; 2-chloro-4-nitrophenyl; 3-nitro-4-sulfophenyl; 2,5-dichloro-4-(2'-sulfoethylsulfonamido)phenyl; 2-methanesulfonyl-4-nitrophenyl; 2,4-dinitrophenyl; 2-nitro-4-fluorophenyl; 2-chloro-5nitrophenyl and 3,5-dinitrophenyl.

5. The arylazo chromoionophore of claim 4 wherein Y is H.

6. The arylazo chromoionophore of claim 4 wherein X is potassium.

7. The arylazo chromoionophore of claim 2 wherein R is a five or six membered heteroaromatic ring selected from the group consisting of 2-thiazolyl; 4-methyl-2-thiazolyl; 4-phenyl-2-thiazolyl; 4,5-dimethyl-2-thiazolyl; 4-phenyl-2-thiazolyl; 5-nitro-2-thiazolyl; 5-bromo-2-thiazolyl; 4-carboxymethyl-2-thiazolyl; 5-nitrophenylsulfonyl-2-thiazolyl; 2-pyridyl; 4,6-dimethyl-2-pyridyl; 5-chloro-2-pyridyl; 5-bromo-2-pyridyl; 3-methyl-2-pyridyl; 5-bromo-3-nitro-2-pyridyl; 3-chloro-5-trifluoromethyl-2-pyridyl; 3,5-dichloro-2-pyridyl; 3-nitro-2-pyridyl; 4-pyridyl; 2,5,6-trifluoro-3-chloro-4-pyridyl; 2-methoxy-5-pyridyl; 2,6-dimethoxy-3-pyridyl; 5-nitro-2-pyrimidyl; 4-methyl-2-pyrimidyl; 4,6-dimethyl-2-pyrimidyl; 4,6-dimethoxy-2-pyrimidyl; 4-chloro-6-methyl-2-pyrimidyl; 5-methyl-3-isoxazolyl; 3-methyl-5-isoxazolyl; 3-methyl-5-isothiazolyl; 1-ethyl-5-pyrazolyl; 2-(1,3,4-thiadiazolyl); 5-ethyl-2-(1,3,4-thiadiazolyl) and 3-phenyl-5-(1,2,4-thiadiazolyl).

8. The arylazo chromoionophore of claim 2 wherein R is a fused ring system made up of a five or six membered, substituted or unsubstituted, carbocyclic aromatic or heteroaromatic rings selected from the group consisting of 4-trifluoromethyl-6-chloro-2-benzothiazolyl; 1-napthyl; 6-(2'-hydroxyethyloxy)-2-benzothiazolyl; 6-tert-butyl-2-benzothiazolyl; 4-methyl-5-chloro-2-benzothiazolyl; 4,5-dimethyl-2-benzothiazolyl; 2-benzothiazolyl; 5-fluoro-2-benzothiazolyl; 6-sulfo-2-benzothiazolyl; 5,6-dichloro-2-benzothiazolyl; 2-β-naphthothiazolyl; 4-bromo-6-chloro-2-benzothiazolyl; 4,5-dichloro-2-benzothiazolyl; 6-nitro-2-benzothiazolyl; 4,5,6,7-tetrachloro-2-benzothiazolyl.

9. The aryl chromoionophore of claim 8 wherein Y is H.

10. The aryl chromoionophore of claim 8 wherein X is potassium.

11. The arylazo chromoionophore of claim 2 wherein R is a fused ring system made up of five or six membered, substituted or unsubstituted, carbocyclic aromatic or heteroaromatic rings selected from the group consisting of 1-isoquinolinyl; 5-isoquinolinyl; 6-nitro-5-quinolinyl; 5-chloro-2-benzoxazolyl; 5,6-dimethyl-2-benzothiazolyl; 6-ethoxy-2-benzothiazolyl; 6-fluoro-2benzothiazolyl; 4-methoxy-2-benzothiazolyl; 6-methoxy-2-benzothiazolyl; 4-methyl-2-benzothiazolyl; and 6-methyl-2-benzothiazolyl.

12. The aryl chromoionophore of claim 11 wherein Y is H.

13. The aryl chromoionophore of claim 11 wherein X is potassium.

14. The arylazo chromoionophore of claim 1 wherein Y is H and R is selected from the group consisting of 2-nitrophenyl; 4-nitrophenyl; 2-thiazolyl; 2,4-dinitrophenyl and 2-methanesulfonyl-4-nitrophenyl.

15. The arylazo chromoionophore of claim 1 wherein X is lithium, sodium or potassium.

16. The arylazo chromoionophores of claim 15 wherein X is potassium.

17. A method for the detection of calcium ion in aqueous liquid suspected of containing such ion which method comprises contacting the liquid with a compound of the formula:

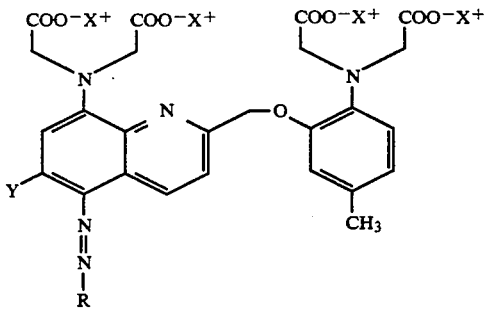

wherein X is hydrogen or a monovalent cation, Y is H or methoxy and R is a ringed aromatic organic structure and determining the optical density change in the liquid resulting from the complexation of calcium ion with said compound.

* * * * *